United States Patent
Valenti et al.

[11] 3,982,279
[45] Sept. 28, 1976

[54] MECHANICAL PROSTHESIS OF THE KNEE

[76] Inventors: Mario Capella Valenti; Jorge Capella Samaranch, both of General Mitre, 188 - 1°, Barcelona-6, Spain

[22] Filed: Mar. 6, 1975

[21] Appl. No.: 556,112

[52] U.S. Cl............................................. 3/27; 3/29
[51] Int. Cl.² ....................... A61F 1/04; A61F 1/08
[58] Field of Search ............................... 3/2, 22–29

[56] References Cited
UNITED STATES PATENTS

| | | | |
|---|---|---|---|
| 1,283,093 | 10/1918 | Critchley | 3/24 |
| 3,694,823 | 10/1972 | May | 3/27 |

FOREIGN PATENTS OR APPLICATIONS

| | | | |
|---|---|---|---|
| 1,169,464 | 11/1969 | United Kingdom | 3/27 |
| 175,193 | 2/1922 | United Kingdom | 3/27 |

*Primary Examiner*—Ronald L. Frinks
*Attorney, Agent, or Firm*—Haseltine, Lake & Waters

[57] ABSTRACT

A mechanical prosthesis of the knee to be locked by a brake system, and formed by the thigh and a leg joined by a brake means pierced by a spindle. In the thigh a drum is integral with an inverted U-shaped support, the base of which is fixed to a rigid member on the thigh. The drum is surrounded by a band open at a single point. Above and below this opening it has two parallel and perforated flat radial lugs pierced by a tie-rod, which is bevelled on its upper portion. This upper portion is threadably engaged with a nut pinned to lock it. The tie-rod has an inverted U-shaped lower portion connected with a lever system having unequal arms. The pivoting point or fulcrum of the lever system is seated on a projection of the band.

5 Claims, 1 Drawing Figure

U.S. Patent  Sept. 28, 1976  3,982,279
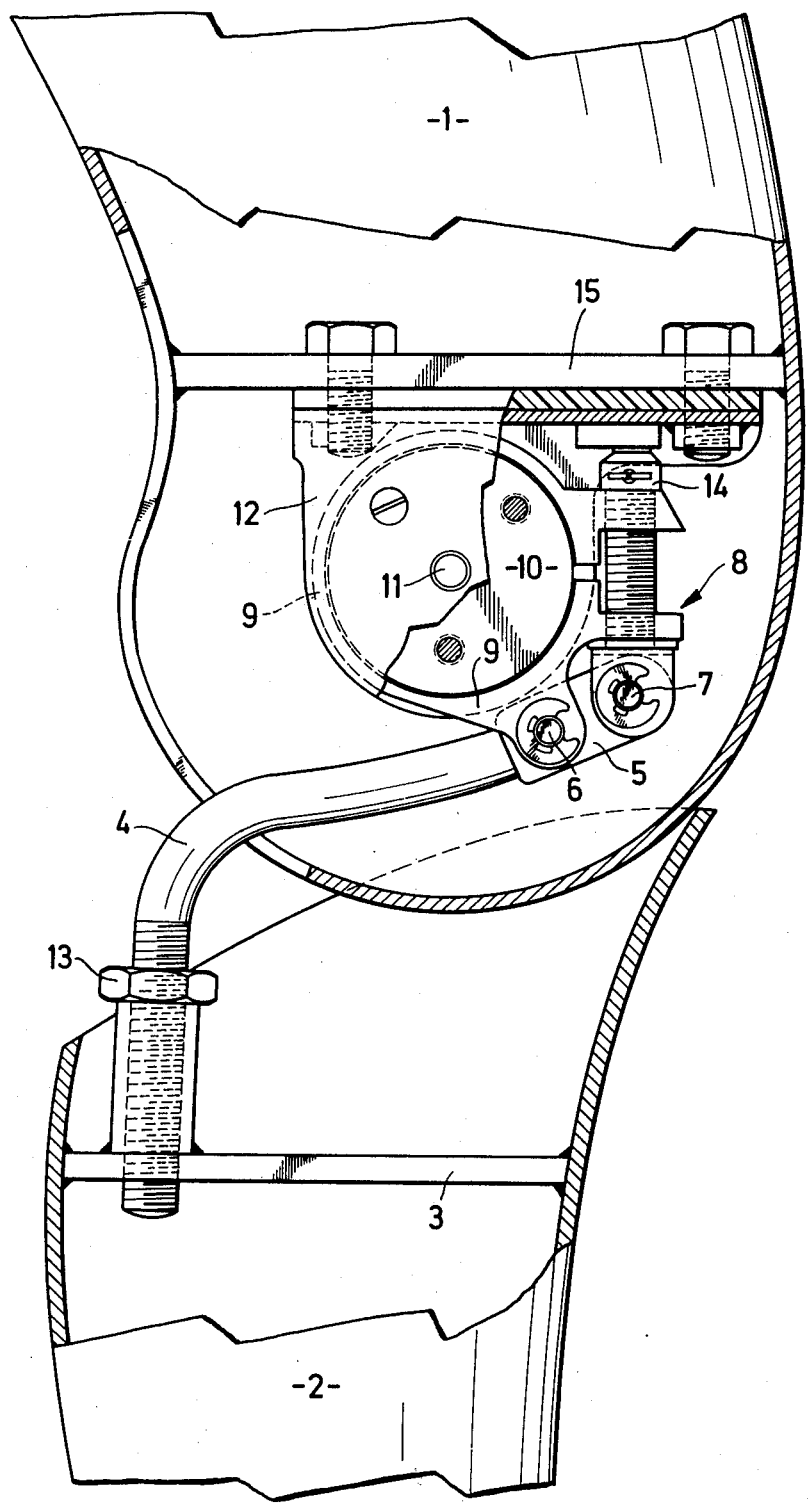

MECHANICAL PROSTHESIS OF THE KNEE

The invention relates to a mechanical prosthesis of the knee, henceforth called an artificial knee, distinguished by having a mechanical device for purposed locking by means of a brake system.

Ordinarily, prostheses of the lower extremities assure the stability of the disabled user by means of what is technically known as "alignment", which is actually nothing other than transfer of the pivot point of the artificial knee to a position behind the axis of load of the disabled user's body since in a physiological man the said axis starts from the centre of movement of the same hip joint, passes vertically through the transverse axis of the knee and terminates in the transverse axis of the ankle. The known technique of transferring the transverse axis of the knee to a point located behind the vertical axis of load of the disabled user's body secures the latter's stability during the action of walking always provided that this be done on a firm and horizontal surface, but should one of these two attributes change, particularly that of levelness, and the disabled user require to advance along a downwards slope, then the said pivot point of the artificial knee will approach ever closer to the axis of load as the slope gets steeper until it eventualy passes beyond the vertical axis of load, which action causes the user of the appliance to lose stability and fall suddenly to the ground.

With a normal man nothing like this occurs since he is in possession of two highly efficient equipments, to wit a strong and rigid framework in the form of his skeleton and a motive system in the form of his musculature, that control not only his stability when standing at rest but also his gait whether walking on the level or on a surface inclined in any direction and thus too on a descending slope.

The present invention opposes the conventional principle of alignment inasmuch as the center of rotation of an artificial knee is situated in the anatomical point of the physiological human being and the contractile action of the muscle is achieved by means of a brake system that operates solely under the action of the load comprised of the weight of the disabled user's body. Thus from the moment when the disabled user puts his foot on the ground, there will be two forces acting in opposite directions. There are the force of gravity and the reaction of the ground. The arrangement assists in securing that the cooperation of these two forces causes the brake system to operate whenever such cooperation prevails but not when it ceases. The moment the disabled user takes the weight off his appliance by lifting his foot off the ground, the knee again swings freely.

In the normal human knee we have two basic movements of unlike potential, namely stretching and bending, the former less intensive than the latter for the ontogenic reason that the flexor muscles are stronger than their extensor counterparts so that the maximum efforts of arms and legs alike are catered for by the flexor as opposed to the extensor groups of muscles. Applying this reasoning to the concrete case here in question, the mechanical artificial knee according to the invention, with its purposed locking by means of a brake system, secures that the function of braking and subsequent locking shall be effected in the postures of flexure of the thigh 1 relative to the leg 2 through the piece 3 when due to displacement of the disabled user's body its weight bears upon the rod 4 which acts on the end of the lever 5 whose fulcrum is at 6 and whose other end 7 acts on the tie-rod 8 which serves to close the band 9 that in turn girdles the drum 10 and locks it, the said drum having its axis in 11 and being integral with the piece 12 which is fixed in turn to 1, while the nuts 13 and 14 provide the means for appropriate regulation and adjustment of the mechanism described.

It is evident therefore from the above description that in the mechanical artificial knee with purposed locking by the action of a brake system, its function of braking and hence locking the joint will take place only and solely in the movement of flexure of the thigh 1 relative to the leg 2 and this moreover only when at the same time the foot (at the end of the leg 2) is resting on the ground and taking the weight of the disabled user's body and that the said function will cease to be operative the moment that this load becomes insufficient to tighten the band 9, from which moment onwards the leg 2 will be entirely free for movements both of flexure and extension. Also meriting detailed mention in view of its considerable functional interest is the fact that, like the flexure of the knee joint in this mechanical prosthesis with purposed locking by means of a brake system according to the invention, the locking is effected always in postures of flexure whereas those of extension are always perfectly free since the only effect exerted by the weight of the disabled user's body is then not to put a load on the brake band but, on the contrary, to ease it.

In further describing the construction and operation of the present invention, the thigh 1 and the leg 2 are joined by a brake means which is pierced by a spindle 11. In the thigh 1, there is provided a drum 10 which is integral with an inverted U-shaped support 12 having a base which is fixed to a member 15 on the thigh 1. The drum 10 is surrounded by a band 9 open at a single location. Above and below this opening of the band 9, the latter has two parallel and perforated flat radial lugs pierced or penetrated by a tie-rod 8. The upper portion of this tie-rod 8 is threadably engaged with a nut 14 which is pinned to the end of the tie-rod for locking it in place. At its inverted U-shaped lower portion 7, the tie-rod is connected to a lever system 4, 5 having unequal arms. The pivoting point or fulcrum of this lever system is seated on a projection 6 of band 9. The short arm 5 is connected with the tie-rod 8 at the portion 7, and the long arm 4 is curved substantially vertically at its rear half, and is threadably engaged with a hexagonal nut 13 resting on a member 3 of the leg 2.

The embodiment hereinover described must be considered as purely a particular case, in no way restrictive, to which may be added any modifications that practice may counsel provided this be done in accord with the basic principles of the invention.

NOTE

Novelty is declared for the contents of the following
We claim:

1. A mechanical prosthesis of a knee with a brake system for locking the knee and comprising a thigh member; a leg member; brake means joining said thigh and leg members and having a drum member in said thigh member; an inverted U-shaped support integral with said drum member, the base of said U-shaped support being fixed to a rigid plate member on said thigh member; a band member surrounding said drum and being open at a single point; two parallel and perforated flat radial lugs on said band and located respectively above and below said opening; a tie-rod passing through said lugs, said tie-rod being bevelled on its upper portion; a nut engaging a threaded portion of said tie-rod on said upper portion of said tie-rod; pin means passing through said nut and said tie-rod to lock said nut to said tie-rod; lever means with unequal arms connected to the lower portion of said tie-rod, said lower portion of said tie-rod being U-shaped, said band having a projection on which said lever means is pivoted, the shorter arm of said lever means being connected with said tie-rod and the longer arm of said lever means being curved at its rear portion to form a substantially vertical portion, said vertical portion of said longer arm being threaded, and a nut engaging the threaded portion of said longer arm and abutting a portion on said leg member.

2. A mechanical prosthesis as defined in claim 1 wherein said brake system comprises a first immobile part including said thigh member and formed by said drum member and said support, said first part forming an anchorage point, a second part of said brake system being formed by said band, said lever means, said projection on said band, said tie-rod, said second part being dependent on the dynamic activity of said leg member.

3. A mechanical prosthesis as defined in claim 1 wherein when said leg member rests on the ground either in erect position or forming an angle with said thigh member, the load received by the pivot of said lever means being transmitted to said tie-rod for closing said band against said drum to block said drum and lock said knee.

4. A mechanical prosthesis as defined in claim 3 wherein the braking intensity of said band on said drum member is controlled by said tie-rod nut in direct relation to the weight to be carried.

5. A mechanical prosthesis as defined in claim 4 wherein the distance of the pivot of said lever means with respect to said plate member is substantially short, said leg member bearing substantially all the functional activity of the knee.

* * * * *